US010321965B2

(12) United States Patent
Ogawa et al.

(10) Patent No.: US 10,321,965 B2
(45) Date of Patent: Jun. 18, 2019

(54) MEDICAL MANIPULATOR SYSTEM AND METHOD FOR CONTROLLING THEREOF

(71) Applicant: OLYMPUS CORPORATION, Tokyo (JP)

(72) Inventors: Ryohei Ogawa, Tokyo (JP); Kosuke Kishi, Tokyo (JP); Keigo Takahashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/597,341

(22) Filed: May 17, 2017

(65) Prior Publication Data
US 2017/0252116 A1 Sep. 7, 2017

Related U.S. Application Data

(63) Continuation of application No. PCT/JP2015/084980, filed on Dec. 14, 2015.

(30) Foreign Application Priority Data

Feb. 3, 2015 (JP) .................................. 2015-018971

(51) Int. Cl.
*A61B 34/00* (2016.01)
*B25J 3/00* (2006.01)
(Continued)

(52) U.S. Cl.
CPC ............... *A61B 34/74* (2016.02); *A61B 34/30* (2016.02); *A61B 34/70* (2016.02); *A61B 34/77* (2016.02);
(Continued)

(58) Field of Classification Search
CPC ....... A61B 90/361; A61B 34/30; A61B 34/37; A61B 1/00193; A61B 34/20
See application file for complete search history.

(56) References Cited

U.S. PATENT DOCUMENTS 5,876,325 A 3/1999 Mizuno et al.
6,364,888 B1 4/2002 Niemeyer et al.
(Continued)

FOREIGN PATENT DOCUMENTS

EP 2 687 181 A1 1/2014
JP S63-100173 U1 6/1988
(Continued)

OTHER PUBLICATIONS

Japanese Office Action dated Sep. 14, 2016 received in JP 2016-548386.
(Continued)

*Primary Examiner* — Shawki S Ismail
*Assistant Examiner* — Zoheb S Imtiaz
(74) *Attorney, Agent, or Firm* — Scully, Scott, Murphy & Presser, P.C.

(57) ABSTRACT

A medical manipulator system including: a medical manipulator having a joint; an operating section having an operating system; and a control unit controlling the medical manipulator according to an operation applied to the operating section. The operating section includes a switch enters or releases a command. The control unit determines whether a deviation between the joint and the operating system exceeds a threshold while the command is entered, carries out a first motion for moving the joint by a displacement corresponding to the displacement of the operating system if the deviation is equal to or smaller than the threshold, carries out a second motion for approaching the joint to the operating system angle if the deviation exceeds the threshold, and stops the motion for approaching the joint to the operating system angle when the command is released when the deviation exceeds the threshold.

11 Claims, 15 Drawing Sheets

(51) Int. Cl.
*G06F 3/01* (2006.01)
*B25J 9/16* (2006.01)
*A61B 34/30* (2016.01)
*A61B 1/00* (2006.01)
*A61B 17/00* (2006.01)
*A61B 90/00* (2016.01)

(52) U.S. Cl.
CPC .............. *B25J 3/00* (2013.01); *B25J 9/1674* (2013.01); *B25J 9/1689* (2013.01); *G06F 3/01* (2013.01); *A61B 1/00149* (2013.01); *A61B 2017/00367* (2013.01); *A61B 2090/067* (2016.02); *G05B 2219/45118* (2013.01)

(56) References Cited

U.S. PATENT DOCUMENTS

| | | | |
|---|---|---|---|
| 8,423,186 | B2 | 4/2013 | Itkowitz et al. |
| 2003/0033024 | A1 | 2/2003 | Sunaoshi |
| 2007/0142825 | A1* | 6/2007 | Prisco .................... B25J 9/1674 606/1 |
| 2008/0234866 | A1 | 9/2008 | Kishi et al. |
| 2009/0163948 | A1 | 6/2009 | Sunaoshi et al. |
| 2010/0274087 | A1* | 10/2010 | Diolaiti ................. A61B 90/37 600/118 |
| 2010/0332031 | A1 | 12/2010 | Itkowitz et al. |
| 2011/0295268 | A1* | 12/2011 | Roelle .................... B25J 9/1689 606/130 |
| 2012/0239058 | A1 | 9/2012 | Namiki |
| 2013/0211590 | A1 | 8/2013 | Diolaiti et al. |
| 2014/0148950 | A1 | 5/2014 | Ogawa et al. |
| 2014/0297130 | A1* | 10/2014 | Griffiths .................. B25J 5/007 701/42 |
| 2016/0166344 | A1 | 6/2016 | Prisco et al. |
| 2017/0129108 | A1 | 5/2017 | Diolaiti et al. |
| 2017/0156806 | A1 | 6/2017 | Prisco et al. |
| 2017/0215977 | A1* | 8/2017 | Saraliev ................ A61B 34/71 |

FOREIGN PATENT DOCUMENTS

| | | |
|---|---|---|
| JP | H07-328016 A | 12/1995 |
| JP | H08-215204 A | 8/1996 |
| JP | 2001-334481 A | 12/2001 |
| JP | 2003-053685 A | 2/2003 |
| JP | 2005-349563 A | 12/2005 |
| JP | 2008-228967 A | 10/2008 |
| JP | 2009-148859 A | 7/2009 |
| JP | 2012-192004 A | 10/2012 |
| JP | 2013-034851 A | 2/2013 |
| JP | 2018-034017 A | 3/2018 |
| WO | 2007/11179 A2 | 10/2007 |
| WO | 2013/123310 A1 | 8/2013 |

OTHER PUBLICATIONS

International Search Report dated Mar. 1, 2016 issued in PCT/JP2015/084980.
Extended Supplementary European Search Report dated Sep. 3, 2018 in European Patent Application No. 15 88 1215.6.

* cited by examiner

MEDICAL MANIPULATOR SYSTEM AND METHOD FOR CONTROLLING THEREOF

CROSS-REFERENCE TO RELATED APPLICATIONS

This is a continuation of International Application PCT/JP2015/084980, with an international filing date of Dec. 14, 2015, which is hereby incorporated by reference herein in its entirety. This application claims the benefit of Japanese Patent Application No. 2015-018971, filed on Feb. 3, 2015, the content of which is incorporated herein by reference.

TECHNICAL FIELD

The present invention relates to a medical manipulator system and a method for controlling thereof.

BACKGROUND ART

There is a known manipulator system that is provided with a motor on a master device side and that employs a master/slave method in which, if a difference in position/orientation arises between a master device and a slave device, then the master device side is driven so as to conform to the slave device while the slave device is immobilized (refer to, for example, Patent Literature 1).

There is also a known manipulator system that is not provided with a motor on the master device side and that employs a master/slave method in which a slave device is moved by an amount less than the amount specified by a master device when the master device is operated in a direction in which the difference in position/orientation with respect to the slave device is reduced and the slave device is moved as instructed by the master device in other directions, thus gradually eliminating the difference in position/orientation in the course of such an operation (refer to, for example, Patent Literature 2).

CITATION LIST

Patent Literature

{PTL 1}
U.S. Pat. No. 6,364,888
{PTL 2}
U.S. Pat. No. 8,423,186

SUMMARY OF INVENTION

Technical Problem

An object of the present invention is to provide a medical manipulator system and a method for controlling thereof that allow the difference in position/orientation to be eliminated by moving the slave-side medical manipulator as instructed by the operator without having to use a large-scale master-side operating section provided with a motor.

Solution to Problem

One aspect of the present invention is a medical manipulator system including: a medical manipulator having at least one joint; an operating section that has an operating system formed into a shape similar to that of the joint of the medical manipulator, that has a distal-end portion supported by the operating system, and that is operated by an operator gripping the distal-end portion; and a control unit configured to control the medical manipulator according to an operation applied to the operating section, wherein the operating section includes, at the distal-end portion thereof, a switch operated to enter or release a command, and wherein the control unit determines whether or not a deviation between the joint and the operating system exceeds a threshold value in a state where the command resulting from operating the switch is entered, performs control so as to carry out a first motion for moving the joint by a displacement corresponding to the displacement of the operating system if the deviation is equal to or smaller than the threshold value, performs control so as to carry out a second motion for making the joint approach the angle of the operating system if the deviation exceeds the threshold value, and performs control so as to stop the motion for making the joint approach the angle of the operating system when the entry of the command resulting from operating the switch is released in a case where the deviation exceeds the threshold value.

In the above-described aspect, the control unit may performs control so as to maintain the first motion even when the command is released by operating the switch in a case where the deviation is equal to or less than the threshold value.

By doing so, it is possible to prevent the position/orientation-difference eliminating motion from being executed in a case where the position/orientation difference is too small for the operator to perceive the position/orientation difference during operation. Furthermore, when the difference in position/orientation between the joint of the medical manipulator and the operating system becomes sufficiently small, if not completely eliminated, as a result of the position/orientation-difference eliminating motion, the command resulting from operating the switch can be disabled to stop the position/orientation-difference eliminating motion.

The above-described aspect may include an alarm unit that informs the operator that the deviation has exceeded the threshold value when the control unit determines that the deviation exceeds the threshold value.

By doing so, when the command for a position/orientation-difference eliminating motion is issued by operating the switch, the alarm unit can inform the operator that the difference in position/orientation is too large to perform an eliminating motion.

The above-described aspect may include an alarm unit that informs the operator that the deviation is equal to or less than the threshold value when the control unit determines that the deviation is equal to or smaller than the threshold value in a state where the joint is moved in the second motion.

By doing so, the alarm unit can inform the operator that the difference in position/orientation has been eliminated sufficiently, and the operator can switch to disable the command resulting from operating the switch and enter normal motion quickly.

In the above-described aspect, the medical manipulator may include, at a distal end thereof, a treatment part that is switchable between an ON state, in which the treatment part works on a living body, and an OFF state, in which the treatment part does not work on the living body, and when determining that the deviation exceeds the threshold value and that the treatment part is in the ON state in a state where the command is entered with the switch, the control unit may performs control so that the joint carries out the second motion after switching the treatment part from the ON state to the OFF state.

In the above-described aspect, the operating section may include a clutch switch that interrupts a coupled operation between the operating system of the operating section and the joint of the medical manipulator.

Another aspect of the present invention is a method for controlling a medical manipulator controlled by a control unit according to an operation applied to an operating section, the medical manipulator having at least one joint and the operating section having an operating system formed into a shape similar to that of the joint of the medical manipulator, the method: determining whether or not a deviation between the joint and the operating system exceeds a threshold value in a state where a command is entered with a switch provided on the operating section; moving the joint such that the joint moves by a displacement corresponding to the displacement of the operating system if it is determined that the deviation is equal to or smaller than the threshold value in a state where the command is entered with the switch; moving the joint such that the joint approaches the angle of the operating system if it is determined that the deviation exceeds the threshold value in a state where the command is entered with the switch; and stopping the motion of the joint approaching the angle of the operating system, when the entry of the command resulting from operating the switch is released in a case where it is determined in the determination step that the deviation exceeds the threshold value.

In the above-described aspect, the threshold value in a case where the treatment part is in the ON state may be set to be smaller than the threshold value in a case where the treatment part is in the OFF state.

In the above-described aspect, in the control unit, the engagement of the clutch switch may be maintained even when the command is released by operating the switch in a case where the deviation is equal to or less than the threshold value.

DESCRIPTION OF EMBODIMENTS

A medical manipulator system 1 according to one embodiment of the present invention will now be described with reference to the drawings.

Figure 1:
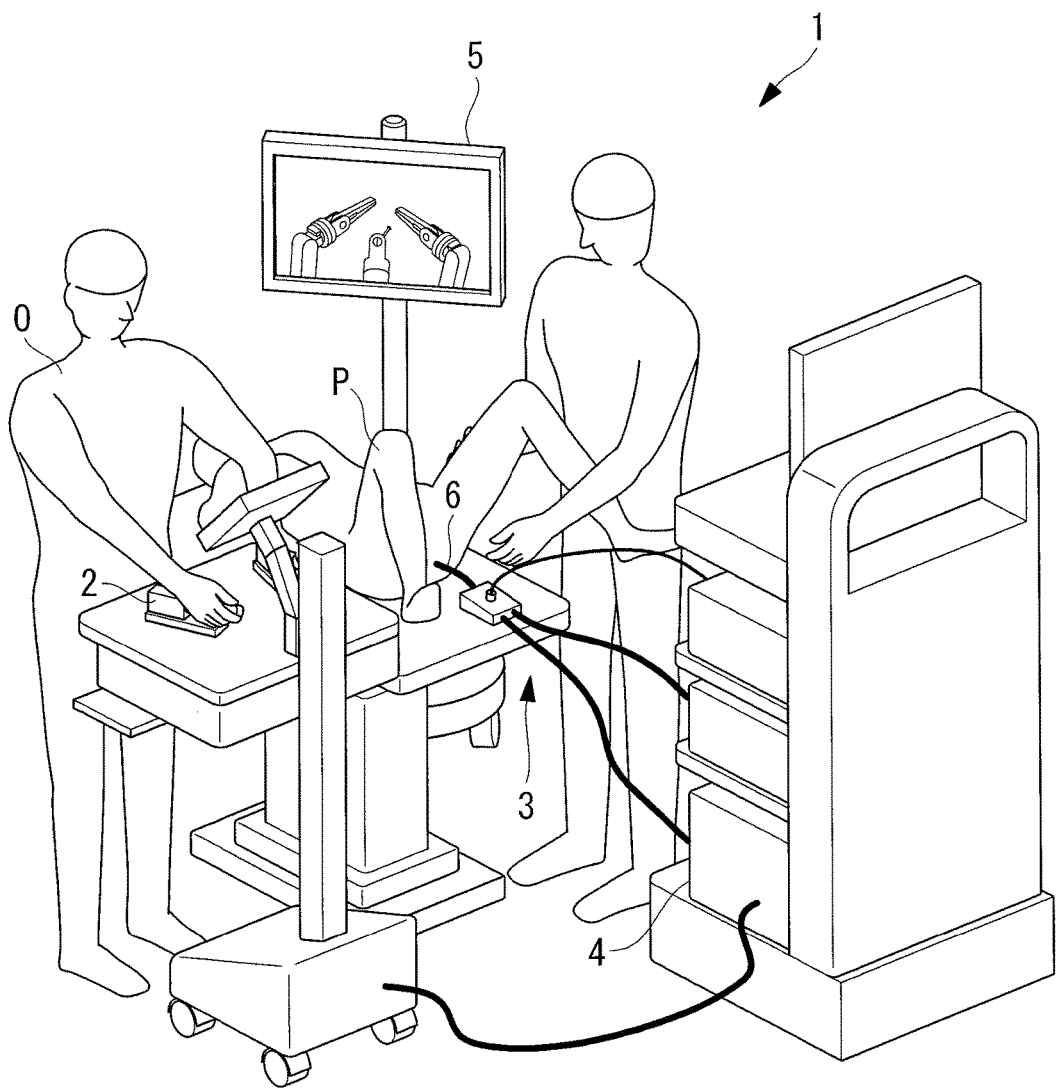
FIG. 1 is an overall configuration diagram showing a medical manipulator system according to one embodiment of the present invention.

As shown in FIG. 1, the medical manipulator system 1 according to this embodiment includes: an operating section 2 that is operated by an operator O; a medical manipulator 3 that is inserted into the body cavity of a patient P; a control unit 4 for controlling the medical manipulator 3 on the basis of the operation of the operating section 2; and a monitor 5.

Figure 2:
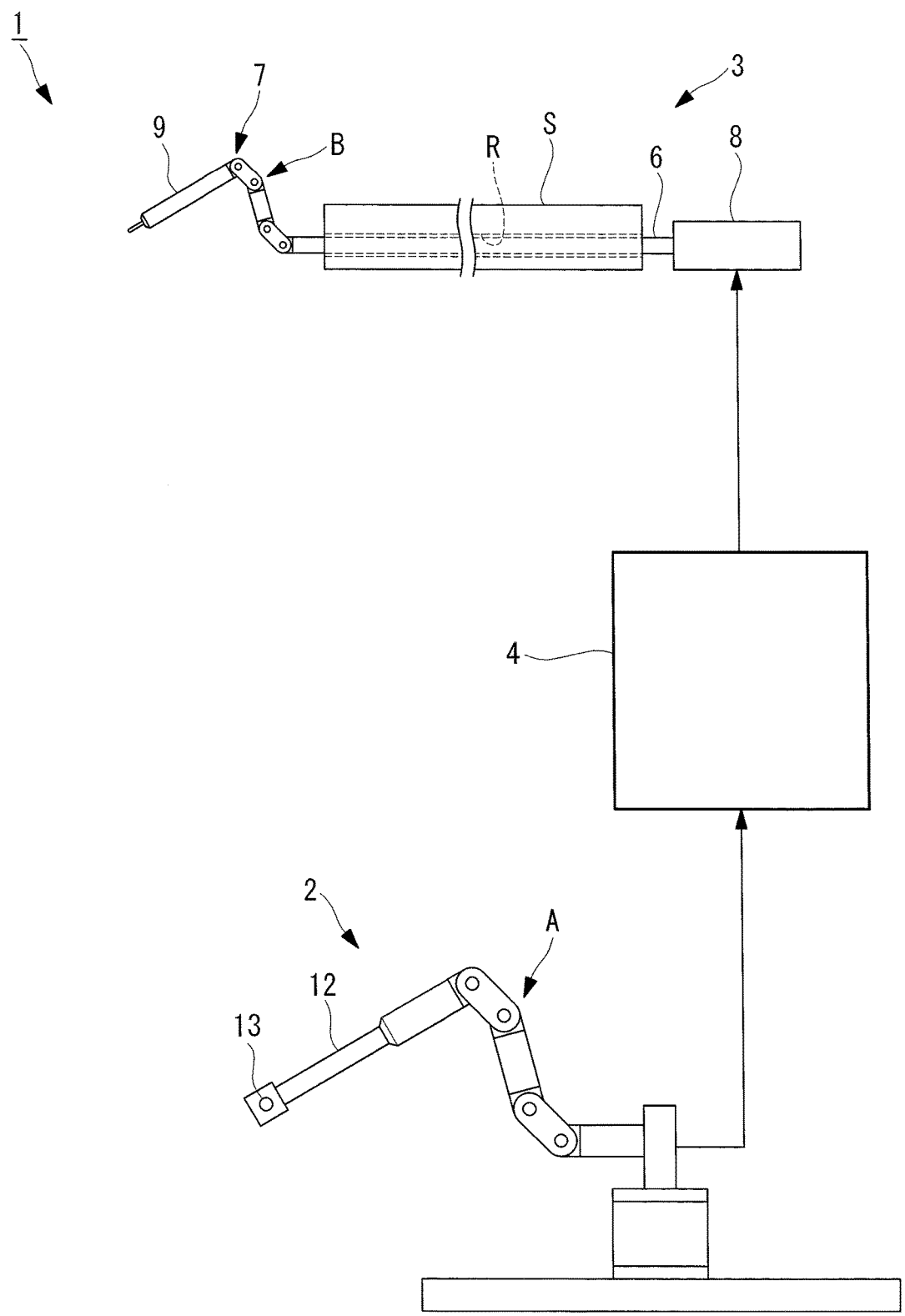
FIG. 2 is a diagram depicting a medical manipulator, an operating section, and a control unit used for the medical manipulator system in FIG. 1.

As shown in, for example, FIG. 2, the medical manipulator 3 includes: an insertion section 6 that is inserted into the body of the patient P via a forceps channel R of an insertion section S of an endoscope to be inserted into the body cavity of the patient P; a movable section 7 provided at the distal end of the insertion section 6; and a drive section 8 that is disposed on the basal end side of the insertion section 6 and that drives the movable section 7 by means of a motive-power transmission member, such as a wire, not shown in the figure.

The movable section 7 includes: a treatment part 9 that is disposed at the most distal end and that works on and treats an affected area in the body; and a plurality of joints B for changing the position/orientation of the distal end of the treatment part 9. The treatment part 9 is, for example, gripping forceps.

The operating section 2 is configured so as to have a similar shape to the medical manipulator 3 and includes a distal-end part 12 supported by the same number of joints (operating systems) A as that in the movable section 7 of the medical manipulator 3. The distal-end part 12 is a part gripped by the operator O and has a switch 13 provided at a distal end portion thereof, and the thumb comes into contact with this distal end portion when the distal-end part 12 is gripped between the thumb and the forefinger of the operator O. The operating section 2 includes sensors, not shown in the figure, for detecting the angles of the joints A constituting the operating section 2, and the outputs of the sensors are sent to the control unit 4.

The switch 13 is, for example, a push-button switch.

Furthermore, the switch 13 also serves as a clutch switch for interrupting a coupled operation between the operating section 2 and the medical manipulator 3.

More specifically, the control unit 4 determines the deviation between each of the joints A in the operating section 2 and the corresponding joint B in the medical manipulator 3 when the switch 13 is pressed and, if the deviation is equal to or less than a predetermined threshold value (the difference in position/orientation is small) for all joints A and B, engages the clutch to cause the operating section 2 and the medical manipulator 3 to be operated in a coupled manner (normal motion mode). At this time, the command for instructing transition to a position/orientation correction mode to be described later, which is issued by operating the switch 13, is disabled, and transition to the position/orientation correction mode is not performed.

Figure 3A:
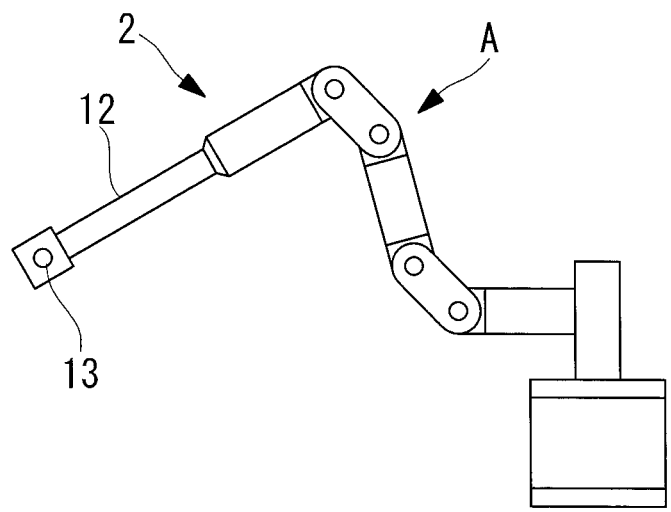
FIG. 3A is a diagram depicting the operating section in a state where a difference in position/orientation arises in the medical manipulator system in FIG. 1.
Figure 3B:
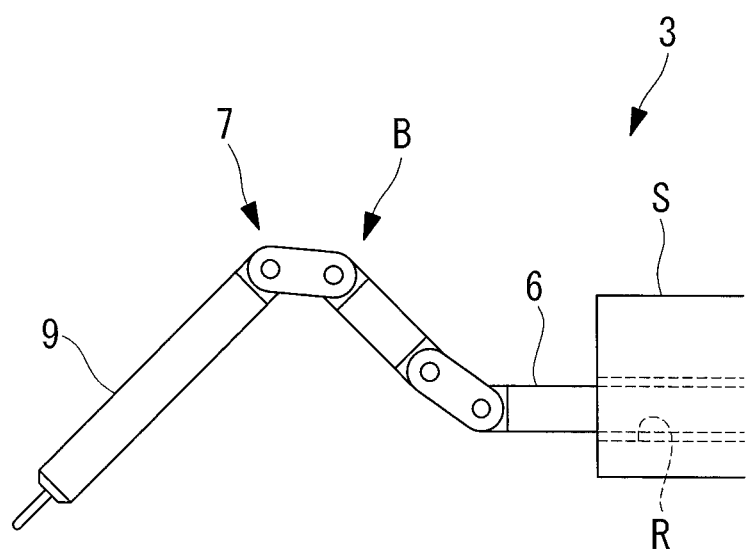
FIG. 3B is a diagram depicting the medical manipulator in a state where a difference in position/orientation arises in the medical manipulator system in FIG. 1.
Figure 4A:
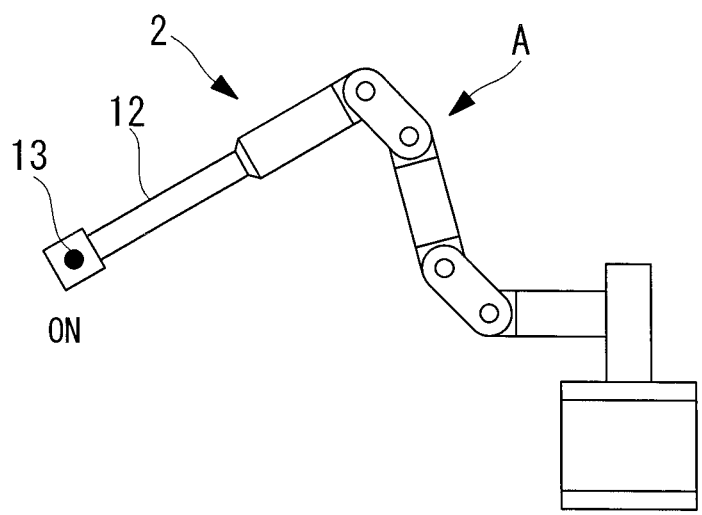
FIG. 4A is a diagram depicting the operating section when a position/orientation correction mode is executed in the medical manipulator system in FIG. 1.
Figure 4B:
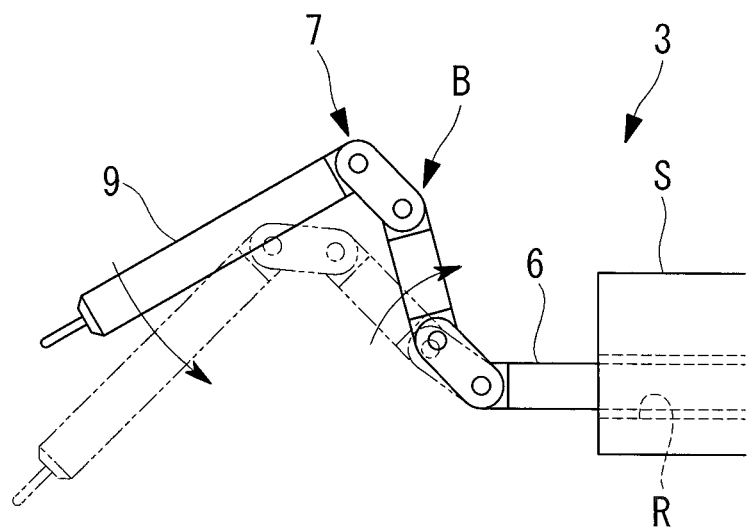
FIG. 4B is a diagram depicting the medical manipulator when the position/orientation correction mode is executed in the medical manipulator system in FIG. 1.

On the other hand, if the deviation of any of the joints B exceeds the threshold value as shown in FIGS. 3A and 3B, then the control unit 4 determines that the command for instructing transition to the position/orientation correction mode, which is issued by operating the switch 13, is enabled, as long as the switch 13 is pressed. Thereafter, as shown in FIGS. 4A and 4B, the control unit 4 moves each of the joints B in the medical manipulator 3 so that the angle of each of the joints B conforms to the angle of the corresponding joint A in the operating section 2 (in the direction in which the difference in position/orientation is eliminated) (position/orientation correction mode).

In this position/orientation correction mode, the control unit 4 moves each of the joints B at a speed equal to or lower than a predetermined speed. The predetermined speed is a speed, for example, equal to one-tenth of the maximum speed in the normal motion mode. The setting of the predetermined speed is optional.

If the angle of each of the joints A in the operating section 2 substantially conforms to the angle of the corresponding joint B in the medical manipulator 3, in other words the deviation is equal to or smaller than the threshold value, while the switch 13 is pressed, then the command resulting from operating the switch 13 is disabled, and the control unit 4 engages the clutch to cause the operating section 2 and the medical manipulator 3 to be operated in a coupled manner (normal motion mode). After the clutch has been engaged, the control unit 4 keeps the clutch engaged even when the operator O releases the switch 13.

In the normal motion mode, in which the clutch is engaged, the control unit 4 moves each of the joints B in the medical manipulator 3 by a displacement equal to the displacement of the corresponding joint A in the operating section 2.

When the switch 13 on the operating section 2 is pressed while the clutch is engaged such that the operating section 2 and the medical manipulator 3 are operated in a coupled manner, the control unit 4 disengages the clutch to release the coupled operation between the operating section 2 and the medical manipulator 3.

A method for controlling the medical manipulator system 1 according to this embodiment with the above-described structure will be described below.

In order to treat an affected area in the body by the use of the medical manipulator system 1 according to this embodiment, the insertion section S of the endoscope is inserted into the body cavity of the patient P, and then the medical manipulator 3 is inserted into the body of the patient P via the forceps channel R of the insertion section S. While the medical manipulator 3 is inserted, the clutch is disengaged so that the coupled operation between the operating section 2 and the medical manipulator 3 is released.

Figure 5:
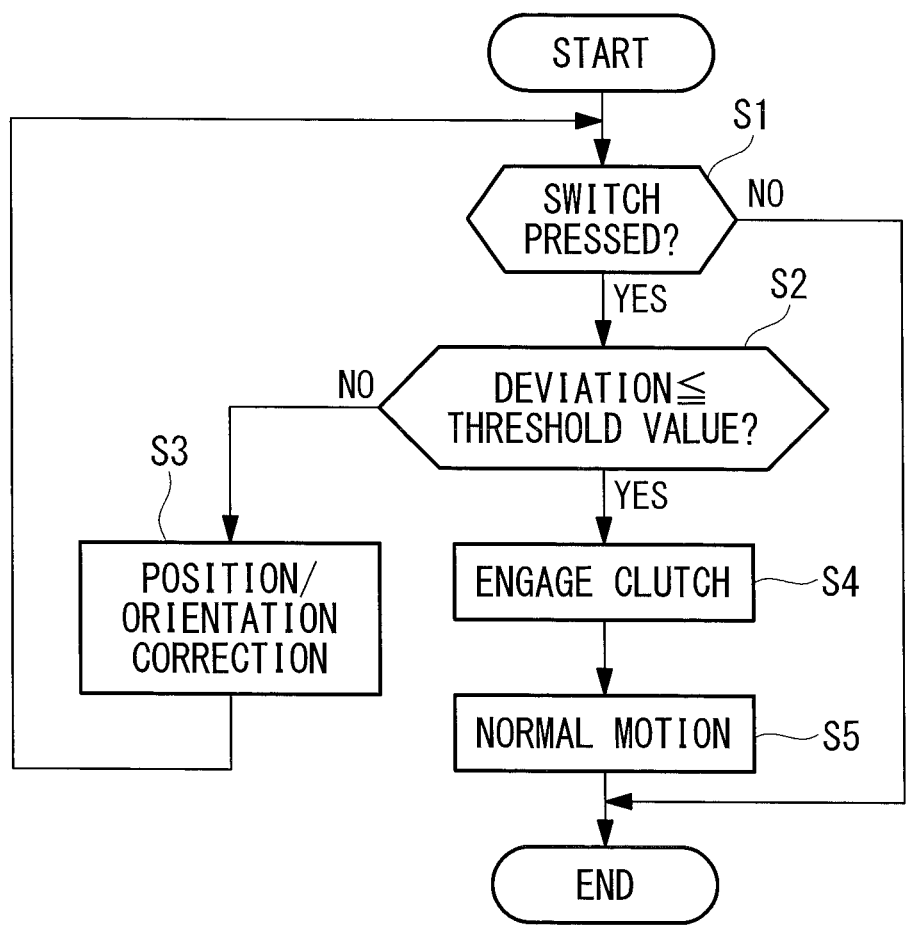
FIG. 5 is a flowchart illustrating a method for controlling the medical manipulator system in FIG. 1.

While observing, on the monitor 5, an image acquired via the endoscope in a state where the movable section 7 at the distal end of the medical manipulator 3 is disposed adjacent to an affected area in the body cavity, the operator O positions the operating section 2 so that the movable section 7 of the medical manipulator 3 and the distal-end part 12 of the operating section 2 take substantially equivalent positions/orientations. When the operator O presses the switch 13 on the operating section 2 in this state, the control unit 4 controls the medical manipulator 3 according to the flowchart shown in FIG. 5.

More specifically, while the switch 13 on the operating section 2 is pressed (step S1), the deviation between each of the joints A in the operating section 2 and the corresponding joint B in the medical manipulator 3 is determined (determination step S2), and, if the deviation of any of the joints B exceeds the predetermined threshold value (a difference in position/orientation exists), then the command resulting from operating the switch 13 is enabled, thus transitioning to the position/orientation correction mode (t1).

Figure 6:
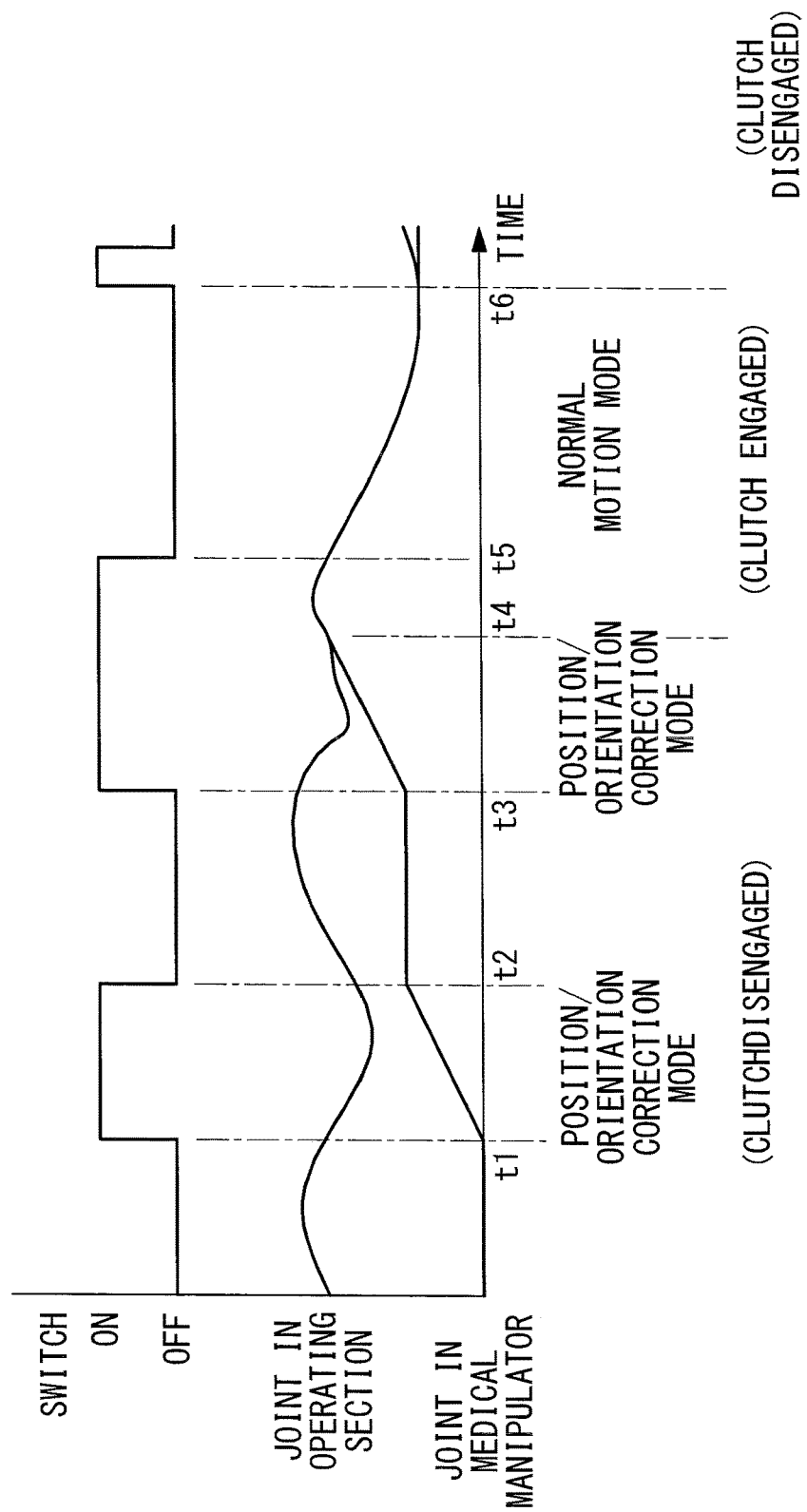
FIG. 6 is a diagram illustrating one example of changes in the state of a switch and the angular position of each joint in the medical manipulator system in FIG. 1.

By doing so, while the switch 13 is pressed, the control unit 4 moves each of the joints B in the medical manipulator 3 at the predetermined speed so that the angle of each of the joints B in the medical manipulator 3 substantially conforms to the angle of the corresponding joint A in the operating section 2 (position/orientation correction step S3). In the position/orientation correction step S3, the angles of the joints B in the medical manipulator 3 approach the angles of the joints A in the operating section 2, as shown in FIG. 6 (FIG. 6 shows only one joint for the sake of simple illustration).

Because this position/orientation correction mode is executed while the switch 13 provided on the operating section 2 is pressed, there is a possibility that each of the joints A in the operating section 2 is moved by the operator O. If that is the case, the corresponding joint B in the medical manipulator 3 moves so as to substantially conform to the new angle of the joint A in the operating section 2. When the operator O releases the switch 13, the position/orientation correction mode is released, and the joints B in the medical manipulator 3 are kept at a standstill, regardless of the motion of each of the joints A in the operating section 2 (t2 to t3).

While each of the joints B in the medical manipulator 3 moves in the position/orientation correction mode, each of the joints B moves at a speed equal to or lower than the predetermined speed, and therefore, the operator O determines whether or not the medical manipulator 3 interferes with surrounding body tissue by checking an endoscopic image on the monitor 5. If there is a risk of interference, the operator O can release the switch 13 to bring the medical manipulator 3 to a standstill, thus avoiding interference.

In this state, the operator O can move the operating section 2 without pressing the switch 13 so that the state of the operating section 2 approaches the state of the medical manipulator 3, and can then press the switch 13 again (t3) to transition to the position/orientation correction mode. In this manner, the operator O can make the angles of the joints B in the medical manipulator 3 approach the angles of the joints A in the operating section 2 while avoiding interference with surrounding body tissue. When the angle of each of the joints B in the medical manipulator 3 substantially conforms to the angle of the corresponding joint A in the operating section 2 (t4), the position/orientation correction mode is released, and the clutch is engaged (step S4) to enter the normal motion mode, in which the operating section 2 and the medical manipulator 3 are operated in a coupled manner.

In other words, because the command resulting from operating the switch 13 is disabled in this state, the operator O thereafter can release the switch 13 at any time while still maintaining the normal motion mode (t5) and hence can operate the medical manipulator 3 without experience any feeling of strangeness in a state where the difference in position/orientation between the operating section 2 and the medical manipulator 3 is eliminated (normal motion step S5).

According to this embodiment, because the operating section 2 does not need to be provided with a motor, no large-scale devices are required, and furthermore, the medical manipulator 3 can be moved as instructed by the operator O who presses the switch 13 to eliminate the differences in position/orientation.

When the coupled operation between the operating section 2 and the medical manipulator 3 is to be released, the clutch can be disengaged by pressing the switch 13 on the operating section 2 again (t6).

Figure 7:
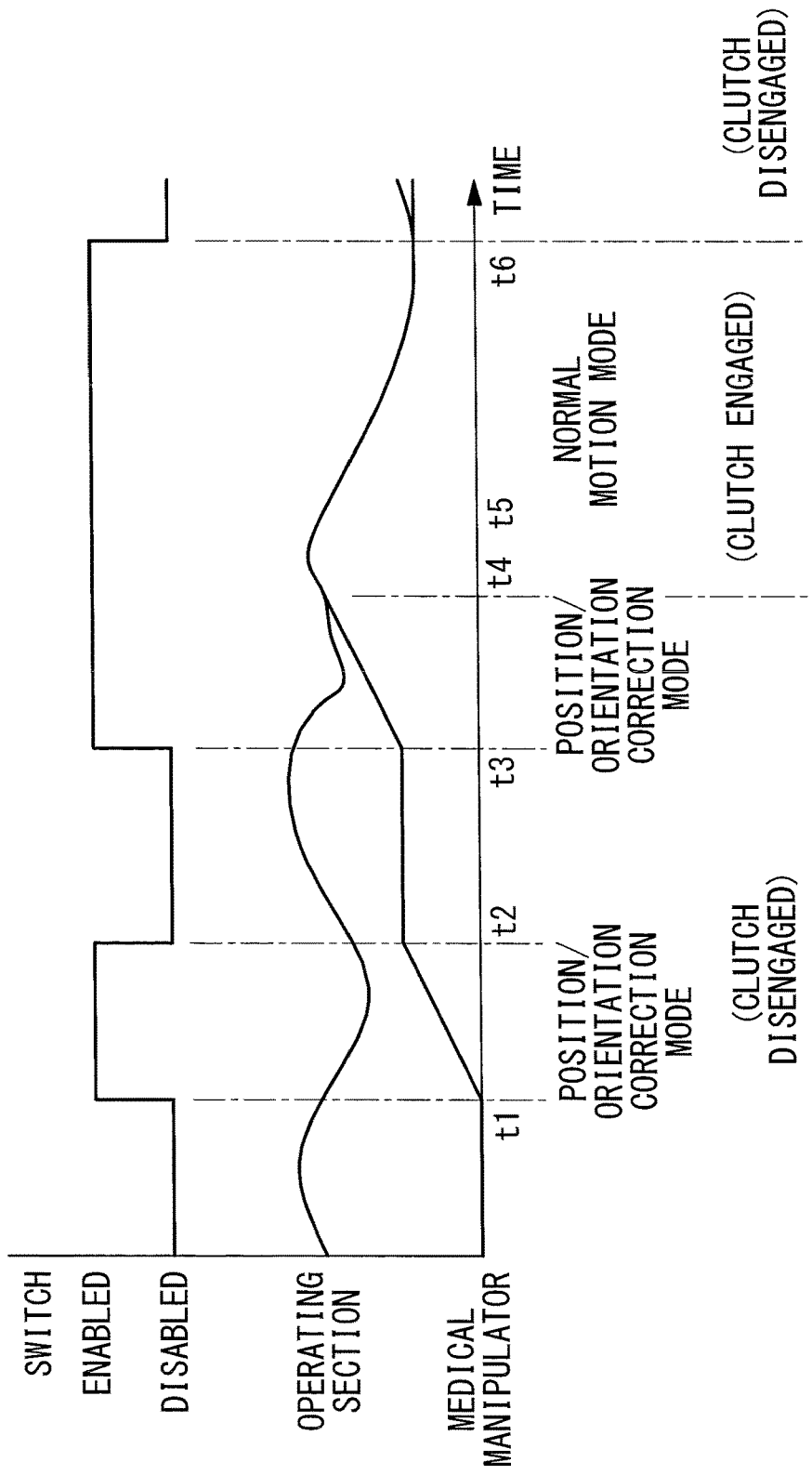
FIG. 7 is a diagram depicting a case where a toggle switch is used as the switch in FIG. 6.

In this embodiment, the motion mode is switched on the basis of the state of the switch 13, as well as the states of the operating section 2 and the medical manipulator 3. Instead of this, a toggle switch for switching between two states, namely the enabled state and the disabled state, may be employed, as shown in FIG. 7.

In this embodiment, the switch 13, which is used to switch to the position/orientation correction mode and which is provided on the operating section 2, is also used as a switch for operating the clutch that interrupts the coupled operation between the operating section 2 and the medical manipulator 3. Instead of this, a switch for the clutch may be provided separately, without serving as the switch 13.

In this embodiment, when the differences in position/orientation are eliminated while the operating section 2 is moving in the position/orientation correction mode, the position/orientation correction mode transitions directly to the normal motion mode. Instead of this, as soon as the differences in position/orientation are eliminated, the operator O may be informed that the normal motion mode has been entered by, for example, displaying something on the monitor (t4). Instead of or in addition to this, the operator O may be informed by means of an alarm (sound).

In this manner, the operator O, even if he or she has insufficient skill to understand that the normal motion mode is entered merely by checking the image on the monitor 5 after the differences in position/orientation have been eliminated, can perceive a mode transition smoothly, regardless of the level of his or her skill.

Figure 8:
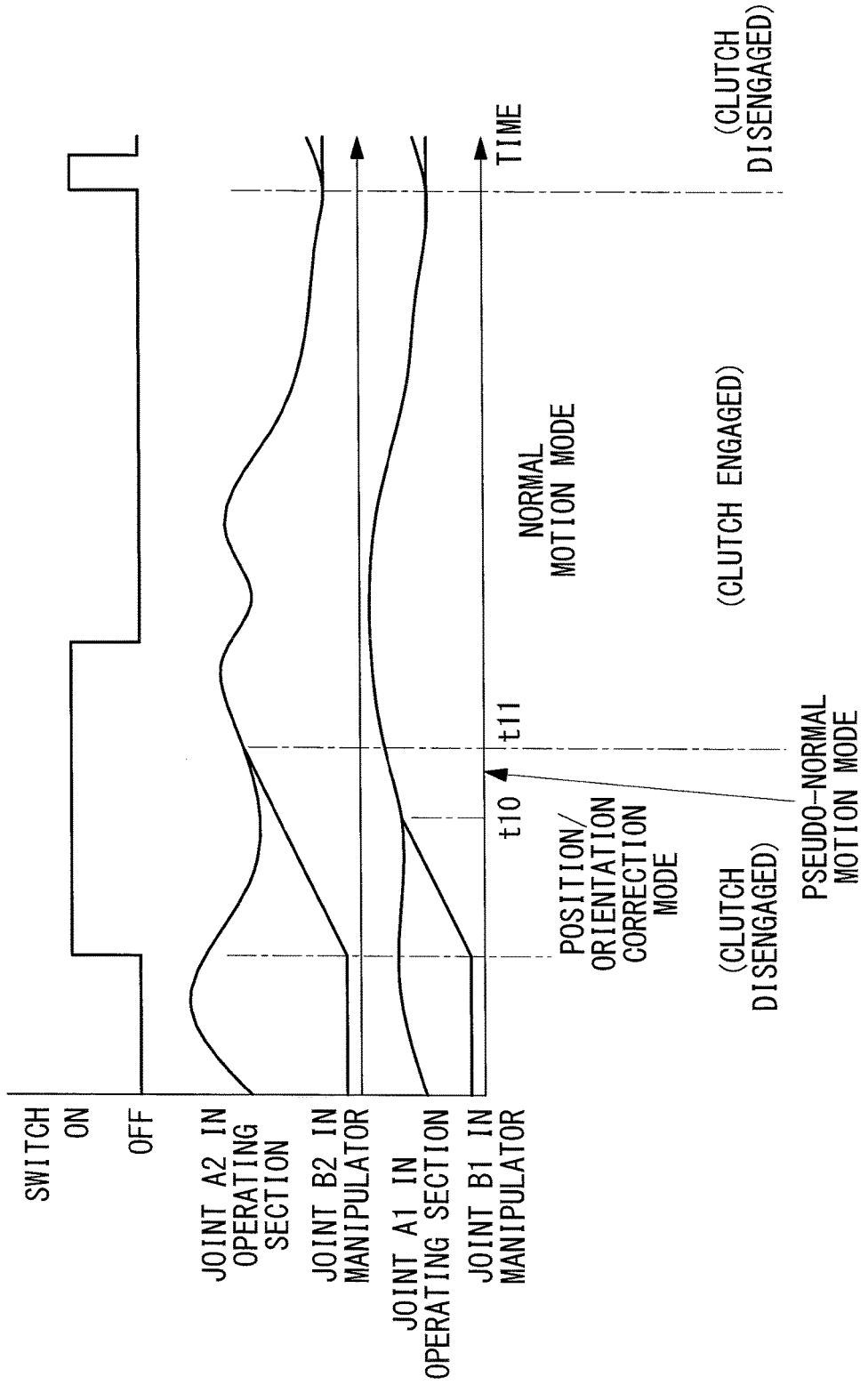
FIG. 8 is a diagram depicting one example of changes in the state of a switch and angular position of each joint in a case where a movable section of the medical manipulator of the medical manipulator system in FIG. 1 is provided with two joints.

This embodiment has been described by way of an example of the motion of only one joint B. However, in a case where the movable section 7 has a plurality of joints B1 and B2, as shown in FIG. 8, it is advisable, as soon as the difference in position/orientation of the joint B1 is eliminated first (t10), to enter a pseudo-normal motion mode, in which the joint B1 is made to follow the motion of the joint A1 in the operating section 2 without engaging the clutch, and thereafter to engage the clutch to enter the normal motion mode as soon as the differences in position/orientation of all the joints A1, A2, B1, and B2 have been eliminated (t11).

Figure 9:
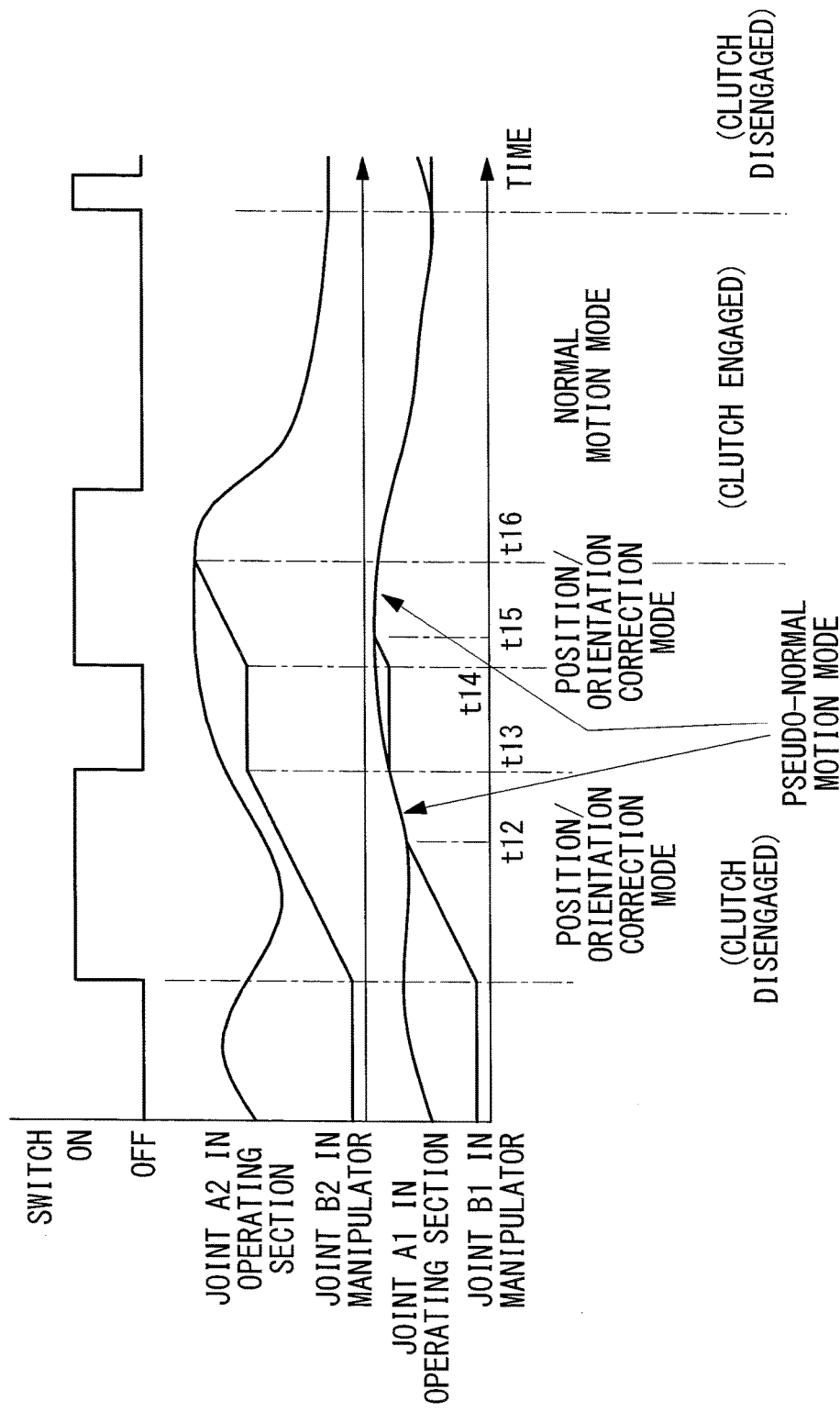
FIG. 9 is a diagram depicting another example of the same motion as in FIG. 8.

FIG. 9 is a diagram illustrating a motion when the operator O releases the switch 13 (t13) in a state where the difference in position/orientation between one pair of the joints A1 and B1 is eliminated (t12) but the difference in position/orientation between another pair of joints A2 and B2 is not eliminated. Because the clutch is not yet engaged the moment the switch 13 is released, all the joints B1 and B2 of the medical manipulator 3 stop, causing differences in position/orientation again. Then, when the switch 13 is pressed again (t14), the position/orientation correction mode resumes. In FIG. 9, the pseudo-normal motion mode is active for the joint B1 in the medical manipulator 3 during the time periods t12 to t13 and t15 to t16, and the clutch is engaged to enter the normal motion mode at the time t16.

Figure 10:
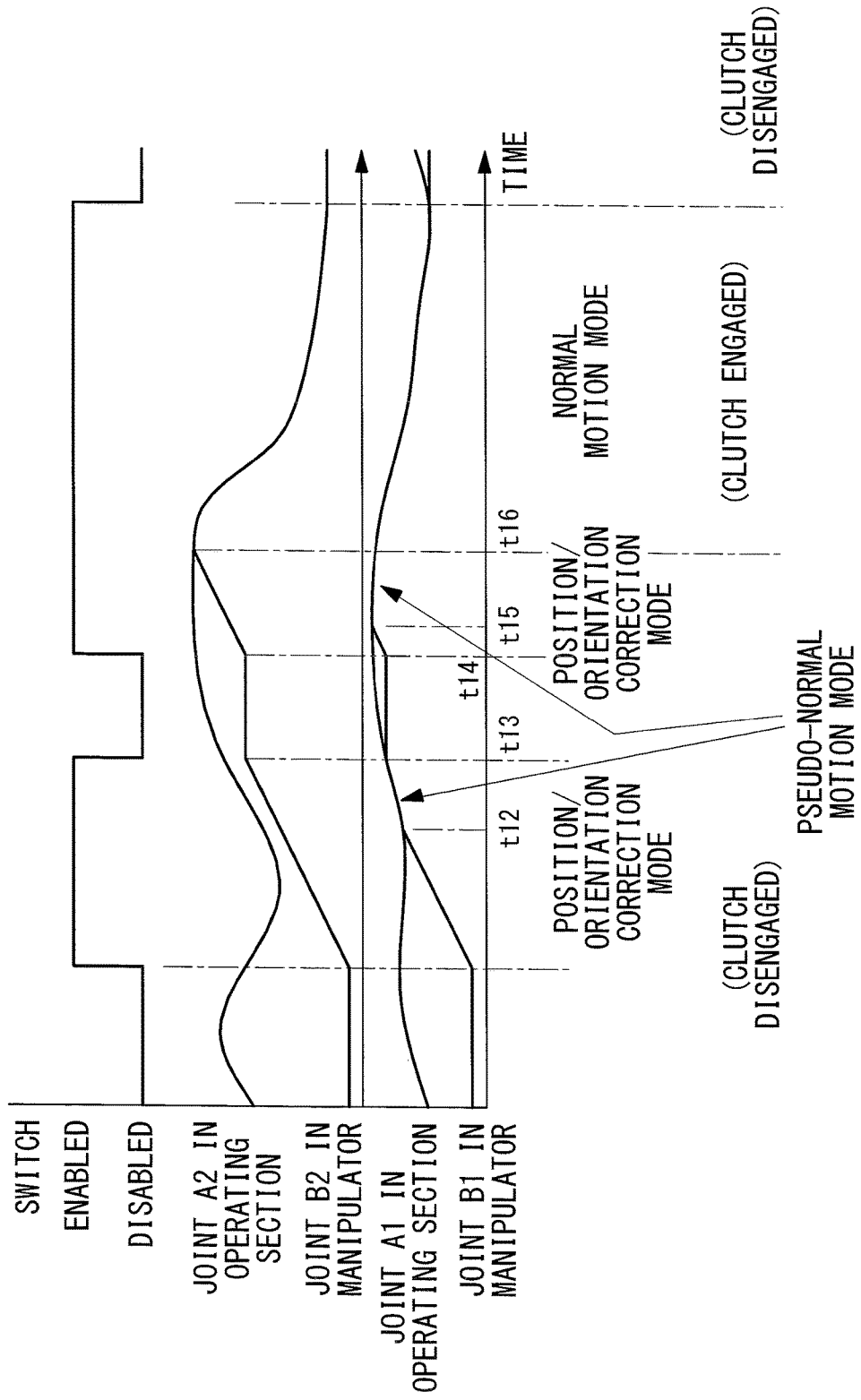
FIG. 10 is a diagram depicting a case where a toggle switch is used as the switch in FIG. 9.

FIG. 10 is a diagram illustrating the same motion in a case where a toggle switch is used.

When the difference in position/orientation between a pair of joints A1 and B1 is eliminated, the pseudo-normal motion mode, in which the motion of the joint B1 in the medical manipulator 3 is made to follow the motion of the joint A1 in the operating section 2 in a state where the clutch is not engaged, is entered. Instead of this, a clutch may be provided for each of the joints B1 and B2, so that the normal motion mode is entered by engaging the clutch, starting with the joints B1 and B2 as soon as the differences in position/orientation of them are eliminated.

Figure 11:
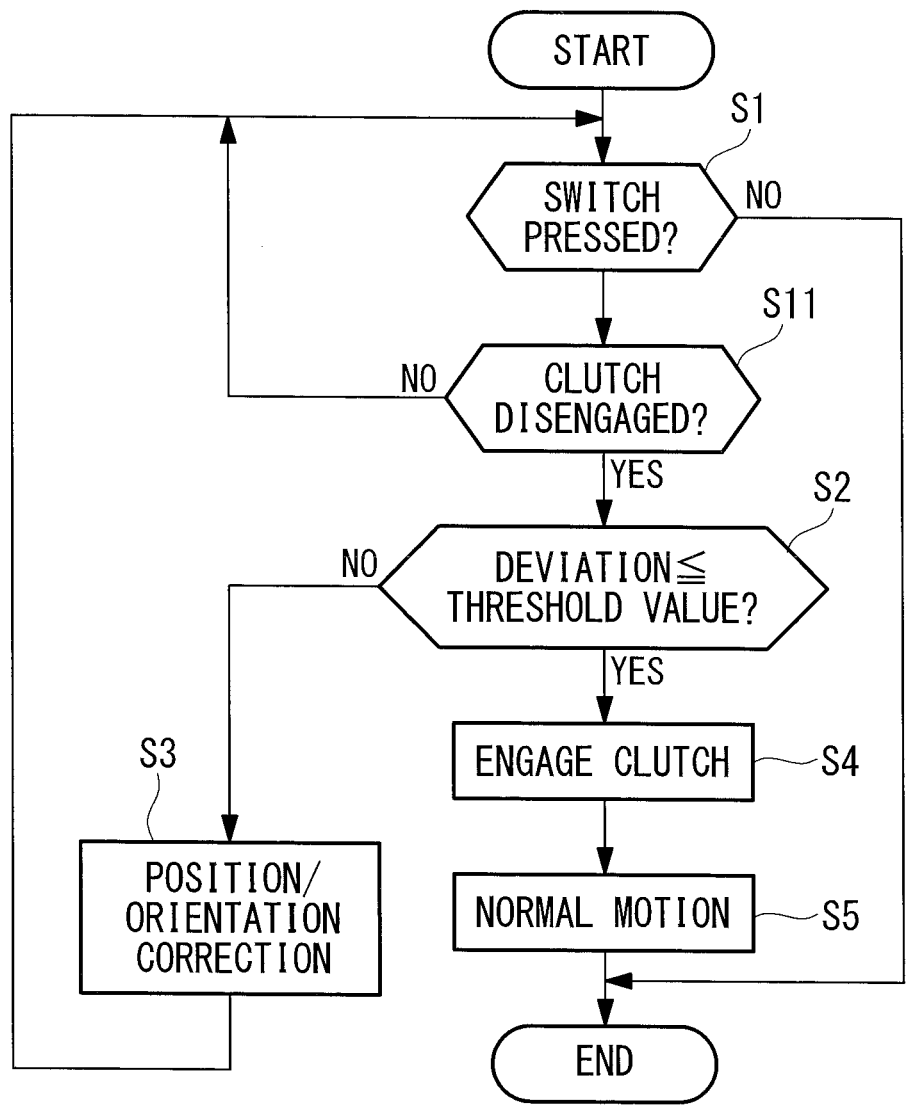
FIG. 11 is a flowchart illustrating a modification of the method for controlling the medical manipulator system in FIG. 1.

As shown in FIG. 11, this embodiment may be such that when the switch 13 is pressed (step S1), it is determined whether or not the coupled operation between the operating section 2 and the medical manipulator 3 is released by the clutch (step S11), so that the position/orientation correction mode can be entered only if the clutch is disengaged. If the operating section 2 and the medical manipulator 3 are operated in a coupled manner in the position/orientation correction mode, the distal end of the medical manipulator 3 moves in an unanticipated direction, which is not desirable. The occurrence of such an inconvenience can be prevented by allowing the position/orientation correction mode to be entered on condition that the coupled operation between the operating section 2 and the medical manipulator 3 is released.

When the angle of each of the joints A in the operating section 2 is changed in a state where each of the joints B in the medical manipulator 3 is moving in the position/orientation correction mode, each of the joints B in the medical manipulator 3 is made to follow a new angular position. However, if the angle of each of the joints A in the operating section 2 is changed to exceed a predetermined threshold value, the position/orientation correction mode may be stopped. By doing so, when the operating section 2 is manually moved by a large distance while position/orientation-difference eliminating motion is in progress, the position/orientation correction mode can be stopped, thereby avoiding contact with surrounding organs etc.

If the deviation between the angle of a joint A in the operating section 2 and the angle of the joint B in the medical manipulator 3 is equal to or more than a predetermined threshold value due to, for example, overload while the medical manipulator 3 is being operated in the normal motion mode, the clutch may be disengaged.

In this embodiment, if the difference in position/orientation arises between a joint A in the operating section 2 and the joint B in the medical manipulator 3 when the switch 13 on the operating section 2 is pressed, the position/orientation correction mode is entered at all times. Instead of this, as shown in FIG. 12, the control unit 4 may monitor the difference in position/orientation between the operating section 2 and the medical manipulator 3 and may determine the deviations between the angles of the joints A in the operating section 2 and the angles of the joints B in the medical manipulator 3 (step S100), so that the position/orientation correction mode can be entered if the determined deviations are equal to or less than a predetermined first threshold value or alarm (alarm unit) may be issued if a determined deviation exceeds the first threshold value (step S101).

The first threshold value is a sufficiently larger value than the threshold value for starting or ending the position/orientation correction mode (referred to as a second threshold value in FIG. 12) in the determination step S2.

If the position/orientation correction mode is allowed to be entered in a case where the deviation between the angle of a joint A in the operating section 2 and the angle of the joint B in the medical manipulator 3 exceeds the predetermined threshold value, the joint B in the medical manipulator 3 moves by a large distance in the position/orientation correction mode. Because of this, when each of the joints B is to be automatically moved with the switch 13, there is a risk of the distal-end portion of the medical manipulator 3 moving in an unanticipated direction, interfering with body tissue. Therefore, in such a case, transition to the position/orientation correction mode can be inhibited, so that transition to the position/orientation correction mode is allowed only after the angles of the joints A in the operating section 2 have been manually made to approach the angles of the joints B in the medical manipulator 3, thus avoiding such interference.

Figure 12:
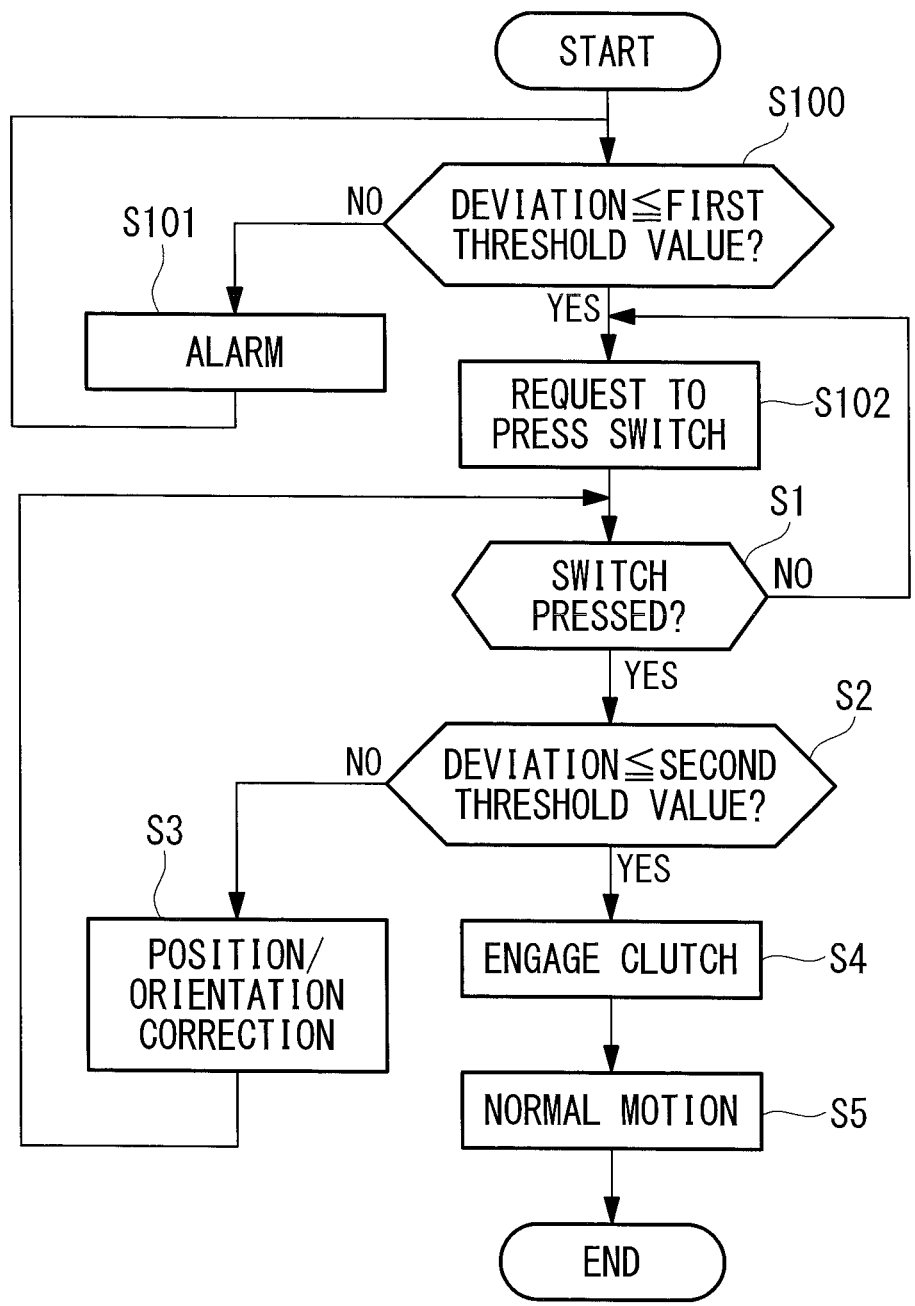
FIG. 12 is a flowchart illustrating another modification of the method for controlling the medical manipulator system in FIG. 1.

What should be pointed out about the alarm in FIG. 12 is that it informs the operator O that a difference in position/orientation is large. In this case, the operator O may be prompted to operate the operating section 2 in the direction in which the difference in position/orientation is reduced.

One example of a method for prompting the operator O to perform such an operation may include displaying on, for example, the monitor 5 in the form of, for example, CG (computer graphics) the position/orientation of the treatment part 9 for which conformance motion is to be performed or the position/orientation of the operating section 2 that should appear when conformance motion has been performed, thereby indicating the direction in which conformance is achieved.

By doing so, even in a case where it is difficult for the operator O to accurately perceive the position/orientation of the treatment part 9, like a case where some joints of the treatment part 9 are outside the endoscopic image, the operator O can be informed of the direction in which the difference in position/orientation will be reduced.

When the deviation of the angle of each of the joints becomes equal to or less than the predetermined first threshold value as a result of the operator O operating the operating section 2 in response to the alarm, it is advisable that the control unit 4 request the operator O to press the switch 13 (step S102).

When the operator O presses the switch 13 in response to the request, the position/orientation correction mode is started with a state where the deviations are small, and this affords an advantage in that the time until the differences in position/orientation are eliminated can be reduced so that the normal motion mode can be entered more quickly. By inhibiting transition to the position/orientation correction mode from a state where a deviation is large, the distal-end portion of the medical manipulator 3 can be prevented from moving in an unanticipated direction, reducing a risk of interference with surrounding body tissue.

If the deviation between the angle of a joint A in the operating section 2 and the angle of the joint B in the medical manipulator 3 exceeds the first threshold value during operation in the normal motion mode, the operator O may be instructed to disengage the clutch to release the coupled operation between the operating section 2 and the medical manipulator 3 and make the angle of each of the joints A in the operating section 2 approach the angle of the corresponding joint B in the medical manipulator 3.

Figure 13:
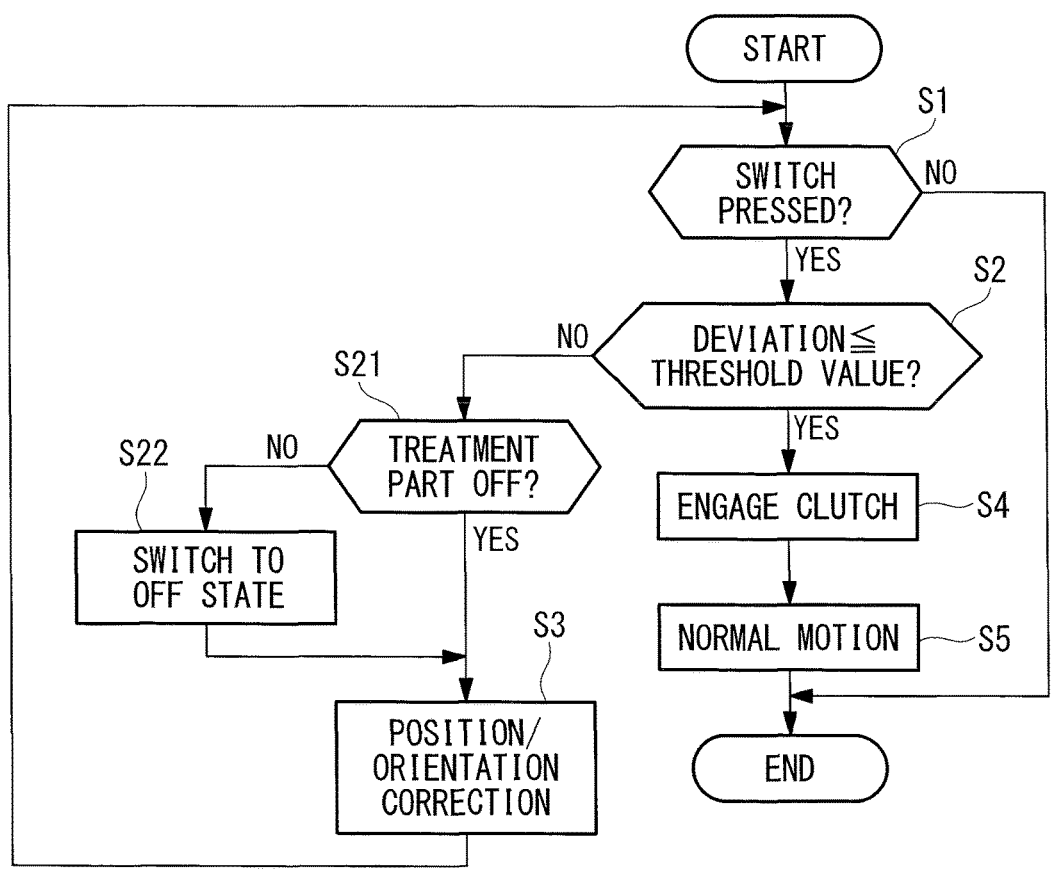
FIG. 13 is a flowchart illustrating another modification of the method for controlling the medical manipulator system in FIG. 1.

As shown in FIG. 13, if a deviation exceeds the threshold value when the switch 13 is pressed, the state of the treatment part 9 provided at the distal end of the medical manipulator 3 may be determined first (step S21), and if the treatment part 9 is in an ON state, then the treatment part 9 may be changed to an OFF state (step S22), and then the position/orientation correction mode may be executed.

The term ON state in this case means a state where the treatment part 9 works on a living body, specifically a state where the distal end is closed to grip the living body in the case of gripping forceps. The term OFF state means a state where the treatment part 9 does not work on a living body, specifically a state where the distal end is open in the case of gripping forceps.

Although gripping forceps are used as an example of the treatment part 9, a stapler, a needle-carrier, scissors, or a suction device, etc. may be employed instead.

In the case of a stapler, a needle-carrier, and scissors, a state where they are closed so as to grip a living body is an ON state and a state where they are open is an OFF state, as in the gripping forceps. In the case of a suction device, a suction state is an ON state, and a non-suction state is an OFF state. Any method, including the gripper method, the lever method, and the push-switch method, can be employed as the operating section 2 for switching ON/OFF the treatment part 9.

In this manner, the position/orientation correction mode is prevented from being entered in an ON state where a stapler, a needle-carrier, or scissors are gripping a living body or in an ON state where a suction device is working on a living body, thereby affording an advantage in preventing the inconvenience that a living body is subjected to stress that could occur if the position/orientation correction mode were entered in an ON state.

Although a device incapable of supplying energy is used as an example of the gripping forceps, a device capable of supplying energy, such as monopolar energy, bipolar energy, or ultrasound, etc., may be employed instead.

In this case, the position/orientation correction mode is executed in a state where the gripping forceps is in an OFF state and no energy is supplied. By doing so, not only is the position/orientation correction mode prevented from being executed in an ON state, but also the position/orientation correction mode is prevented from being executed while energy is being supplied, regardless of the gripping forceps being in an OFF state.

Figure 14:
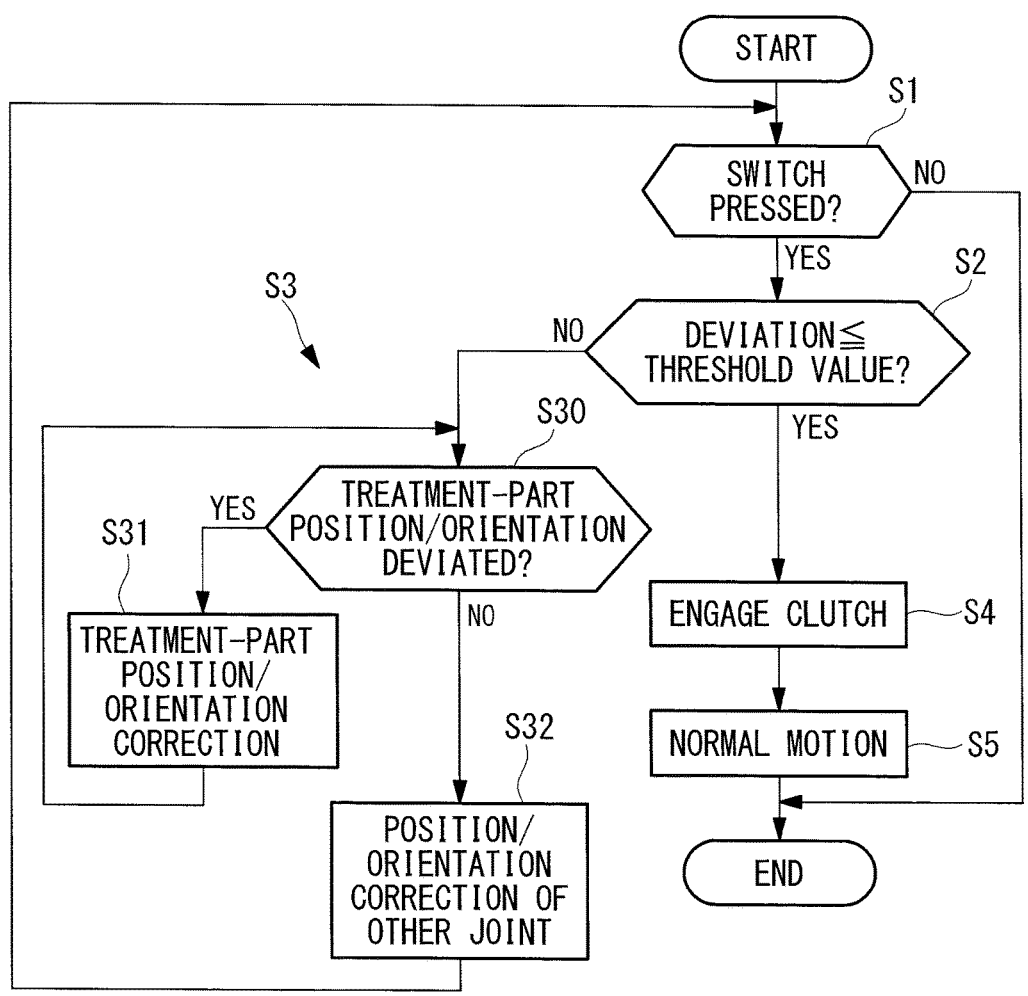
FIG. 14 is a flowchart illustrating another modification of the method for controlling the medical manipulator system in FIG. 1.

When the position/orientation correction mode is started by pressing the switch 13 in a case where the treatment part 9 has at least one joint and the operating section 2 is provided with a joint corresponding to that joint in the treatment part 9, it is preferable that the difference in position/orientation of each of the joints in the treatment part 9 be determined, as shown in FIG. 14 (step S30), and then the differences in position/orientation of the joints in the treatment part 9 be eliminated first (step S31), followed by the elimination of the differences in position/orientation of other joints (step S32).

In this case, the clutch for the joints of the treatment part 9 may be kept engaged at all times. Even while position/orientation-difference eliminating step S32 is in progress in the position/orientation correction mode, the operator can operate the treatment part 9 whenever he or she needs to operate the treatment part 9 displayed on the monitor 5, thus making it possible for the operator O to eliminate the difference in position/orientation between the operating section 2 and the medical manipulator 3 while still preventing the living body from being subjected to stress.

Figure 15:
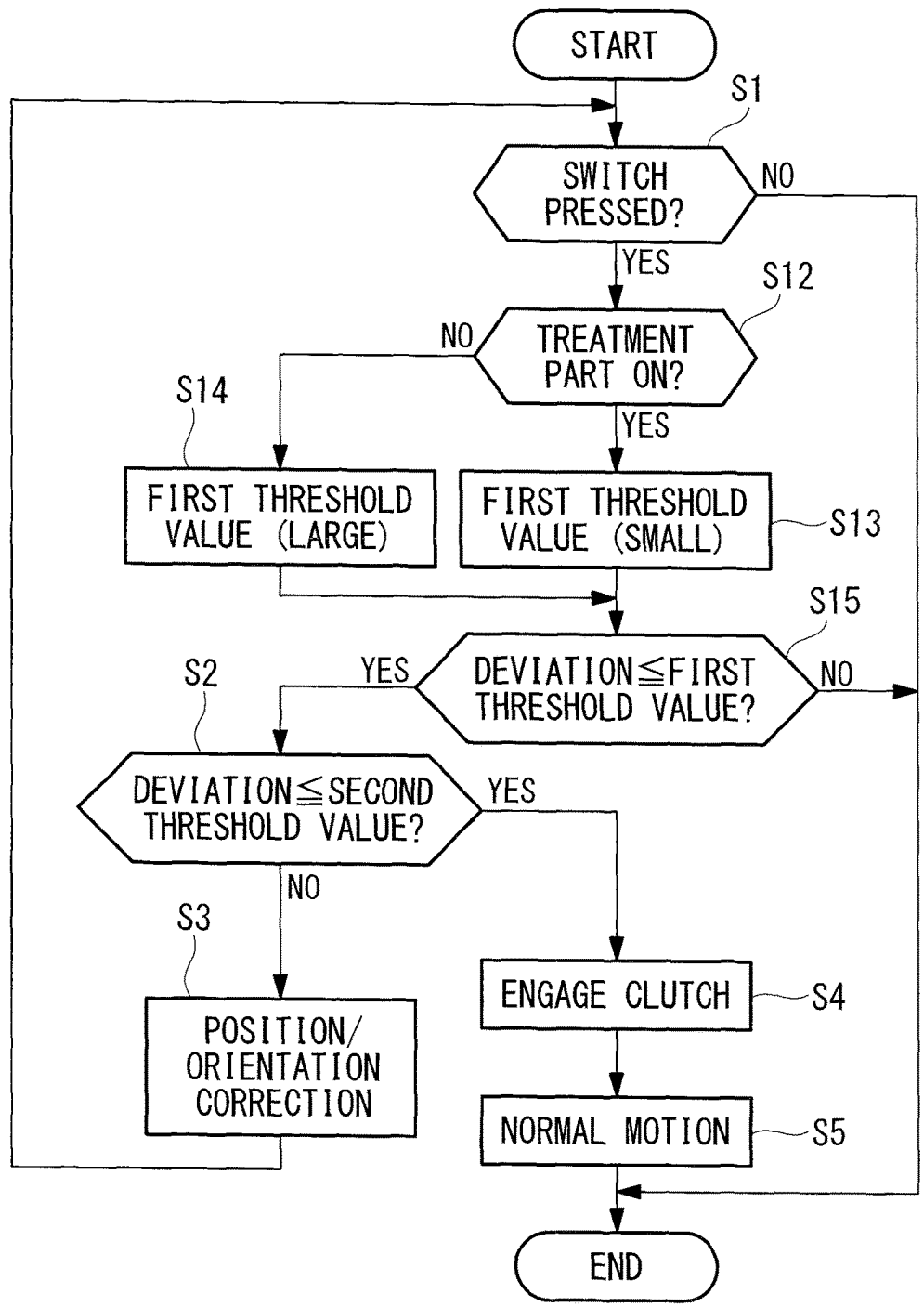
FIG. 15 is a flowchart illustrating another modification of the method for controlling the medical manipulator system in FIG. 1.

The first threshold value used when transitioning to the position/orientation correction mode according to whether the treatment part 9 is in an ON state or in an OFF state may be switched (step S12). As shown in, for example, FIG. 15, it is advisable that the first threshold value be set to be small when the treatment part 9 is in an ON state (step S13) and that the first threshold value be set to be large when the treatment part 9 is in an OFF state (step S14). Then, it is determined whether the deviation between the angle of a joint in the treatment part 9 and the angle of another joint exceeds the set first threshold value (step S15), and transition to the position/orientation correction mode is allowed if the determined deviation is equal to or less than the predetermined first threshold value, or the medical manipulator 3 is stopped if the determined deviation exceeds the first threshold value.

By doing so, transition to the position/orientation correction mode from a state where the difference in position/orientation is large is inhibited while the treatment part 9 is working on the living body, thereby reducing stress to the living body.

In this embodiment, the joints B of the medical manipulator 3 in the position/orientation correction mode are moved at the same speed. Instead of this, the speed may differ for each of the joints B.

In this case, the speed may be variable according to the magnitude of the deviation. By doing so, the position/orientation correction motion of all joints B can be completed at substantially the same time, making it easier for the operator O to perceive the end of the position/orientation correction motion.

In this embodiment, the joints B of the medical manipulator 3 in the position/orientation correction mode are moved at the same time. Instead, the joints B may be moved individually one after another, in order.

For example, the differences in position/orientation may be eliminated in order, starting with the joint B on the base side of the movable section 7. By doing so, the progress of the position/orientation correction mode can be easily checked.

The joints B may be moved in the order in which the distal end of the treatment part 9 does not move by a large distance.

The joints B may be moved in the order in which the maximum distance of each of the joints B from the central axis of the movable section 7 is minimized.

By doing so, interference with surrounding body tissue that could be caused when the movable section 7 is operated can be minimized.

Each of the joints B may be moved at low speed at the initial stage in the position/orientation correction mode and thereafter may be moved at high speed. By doing so, it is possible to check for interference between the movable section 7 and the body tissue at the initial stage of the position/orientation correction mode, and after it has been confirmed that there is no interference, the joints B can be moved at high speed to eliminate the differences in position/orientation in a short time.

This embodiment has been described by way of an example of, but is not limited to, a device having a medical manipulator 3 with a similar shape to the operating section 2. Instead, an operating section of any shape can be employed. If, for example, the medical manipulator 3 and the operating section 2 are structurally different, the amount of driving of each of the joints B may be calculated by solving the inverse kinematics so that the position/orientation of the distal end of the medical manipulator 3 conforms to the position/orientation of the grip section of the operating section 2, thereby achieving conformance between them.

As a result, the following aspect is read from the above described embodiment of the present invention.

One aspect of the present invention is a medical manipulator system including: a medical manipulator having at least one joint; an operating section that has an operating system formed into a shape similar to that of the joint of the medical manipulator, that has a distal-end portion supported by the operating system, and that is operated by an operator gripping the distal-end portion; and a control unit configured to control the medical manipulator according to an operation applied to the operating section, wherein the operating section includes, at the distal-end portion thereof, a switch operated to enter or release a command, and wherein the control unit determines whether or not a deviation between the joint and the operating system exceeds a threshold value in a state where the command resulting from operating the switch is entered, performs control so as to carry out a first motion for moving the joint by a displacement corresponding to the displacement of the operating system if the deviation is equal to or smaller than the threshold value, performs control so as to carry out a second motion for making the joint approach the angle of the operating system if the deviation exceeds the threshold value, and performs control so as to stop the motion for making the joint approach the angle of the operating system when the entry of the command resulting from operating the switch is released in a case where the deviation exceeds the threshold value.

According to the present aspect, as a result of the operator gripping and operating the operating section, the medical manipulator is controlled by the control unit according to the operation. When the operator operates the switch provided on the operating section, the control unit determines whether the command resulting from the operation is enabled or disabled, and if the command resulting from the operation is enabled, a position/orientation-difference eliminating motion for moving the joint of the medical manipulator in the direction in which the difference in position/orientation with respect to the operating system of the operating section is eliminated is performed. At this time, the operator operates the switch for the purpose of eliminating the difference in position/orientation, and according to the command resulting from this operation, the difference in position/orientation is eliminated.

On the other hand, if the command resulting from operating the switch is disabled, the position/orientation-difference eliminating motion is stopped.

In other words, according to the present aspect, because the medical manipulator, serving as a slave side, is moved, it is not necessary that the operating section, serving as a master side, be provided with a motor. This allows the device to be compact and less costly. In addition, because the motion of the medical manipulator is switched as a result of the operator intentionally operating the switch, the operator can move the medical manipulator as desired to eliminate the difference in position/orientation without feeling strange.

The treatment part is made to conform to the operating system of the operating section before the start of a position/orientation-difference eliminating motion in which the joint of the medical manipulator is moved, thereby minimizing interference between the treatment part and the living body during the eliminating motion.

In the above-described aspect, the control unit may performs control so as to maintain the first motion even when the command is released by operating the switch in a case where the deviation is equal to or less than the threshold value.

By doing so, it is possible to prevent the position/orientation-difference eliminating motion from being executed in a case where the position/orientation difference is too small for the operator to perceive the position/orientation difference during operation. Furthermore, when the difference in position/orientation between the joint of the medical manipulator and the operating system becomes sufficiently small, if not completely eliminated, as a result of the position/orientation-difference eliminating motion, the command resulting from operating the switch can be disabled to stop the position/orientation-difference eliminating motion.

The above-described aspect may include an alarm unit that informs the operator that the deviation has exceeded the threshold value when the control unit determines that the deviation exceeds the threshold value.

By doing so, when the command for a position/orientation-difference eliminating motion is issued by operating the switch, the alarm unit can inform the operator that the difference in position/orientation is too large to perform an eliminating motion.

The above-described aspect may include an alarm unit that informs the operator that the deviation is equal to or less than the threshold value when the control unit determines that the deviation is equal to or smaller than the threshold value in a state where the joint is moved in the second motion.

By doing so, the alarm unit can inform the operator that the difference in position/orientation has been eliminated sufficiently, and the operator can switch to disable the command resulting from operating the switch and enter normal motion quickly.

In the above-described aspect, the medical manipulator may include, at a distal end thereof, a treatment part that is switchable between an ON state, in which the treatment part works on a living body, and an OFF state, in which the treatment part does not work on the living body, and when determining that the deviation exceeds the threshold value and that the treatment part is in the ON state in a state where the command is entered with the switch, the control unit may performs control so that the joint carries out the second motion after switching the treatment part from the ON state to the OFF state.

In this manner, the treatment part is switched to the OFF state before the joint is moved when the command for a position/orientation-difference eliminating motion is issued by operating the switch in a state where the treatment part is in the ON state and is treating the living body, thereby minimizing interference between the treatment part and the living body during the position/orientation-difference eliminating motion.

In the above-described aspect, the operating section may include a clutch switch that interrupts a coupled operation between the operating system of the operating section and the joint of the medical manipulator.

By doing so, the operator can operate the clutch switch to release the coupled operation between the operating system of the operating section and the joint of the medical manipulator and disable the command resulting from operating the switch, thereby performing a motion for reducing the difference in position/orientation without moving the medical manipulator. Thereafter, the operator can direct the execution of a position/orientation-difference eliminating motion by switching the command resulting from operating the switch to the enabled state to eliminate the difference in position/orientation with a small displacement of the medical manipulator, thereby minimizing interference with the surrounding living body. At this time, when the command resulting from operating the switch is switched to the disabled state as a result of, for example, the operator releasing the switch, the position/orientation-difference eliminating motion is stopped and the control from the operating section is disconnected, thus making it possible to stop the motion of the joint of the medical manipulator.

Another aspect of the present invention is a method for controlling a medical manipulator controlled by a control unit according to an operation applied to an operating section, the medical manipulator having at least one joint and the operating section having an operating system formed into a shape similar to that of the joint of the medical manipulator, the method: determining whether or not a deviation between the joint and the operating system exceeds a threshold value in a state where a command is entered with a switch provided on the operating section; moving the joint such that the joint moves by a displacement corresponding to the displacement of the operating system if it is determined that the deviation is equal to or smaller than the threshold value in a state where the command is entered with the switch; moving the joint such that the joint approaches the angle of the operating system if it is determined that the deviation exceeds the threshold value in a state where the command is entered with the switch; and stopping the motion of the joint approaching the angle of the operating system, when the entry of the command resulting from operating the switch is released in a case where it is determined that the deviation exceeds the threshold value.

In the above-described aspect, the threshold value in a case where the treatment part is in the ON state may be set to be smaller than the threshold value in a case where the treatment part is in the OFF state.

In the above-described aspect, in the control unit, the engagement of the clutch switch may be maintained even when the command is released by operating the switch in a case where the deviation is equal to or less than the threshold value.

REFERENCE SIGNS LIST

1 Medical manipulator system
2 Operating section
3 Medical manipulator
4 Control unit
9 Treatment part
13 Switch
A, A1, A2 Joints (operating systems) of operating section
B, B1, B2 Joints of medical manipulator
O Operator
P Patient
S2 Determination step
S3 Position/orientation correction step
S5 Normal motion step

The invention claimed is:

1. A medical manipulator system comprising:
 a medical manipulator having:
  at least one first joint; and
  a treatment part provided at a distal end of the medical manipulator, the treatment part being configured to work on living tissue;
 an operation section having at least one second joint corresponding to the at least one first joint; and a controller configured to control the medical manipulator according to an operation applied to the operating section, the controller having:
a first mode configured to carry out a first motion for moving the at least one first joint by a displacement corresponding to the displacement of the at least one second joint; and
a second mode configured to carry out a second motion for eliminating a difference between an angle of the first joint and an angle of the second joint which corresponds to the first joint;
wherein the controller is configured to:
receive a signal so as to switch from the first mode to the second mode;
calculate a deviation between the at least one first joint and the at least one second joint; and
receive an indication as to whether or not the treatment part is working on living tissue;
wherein when the calculated deviation exceeds a threshold value and the indication indicates that the treatment part is not working on the living tissue, the controller is further configured to:
switch from the first mode to the second mode; and
execute the second mode;
when the indication indicates that the treatment part is working on the living tissue, the controller is configured to set the threshold value to a first value;
when the indication indicates that the treatment part is not working on the living tissue, the controller is configured to set the threshold value to a second value, the second value being larger than the first value; and
where the deviation exceeds the threshold value, the controller is configured to:
switch from the first mode to the second mode; and
execute the second mode.

2. The medical manipulator system according to claim 1, further comprising:
a switch configured to generate the signal by being actuated;
wherein the controller is configured to:
where the calculated deviation exceeds a threshold value, the indication indicates that the treatment part is not working on the living tissue and the switch is being actuated:
switch from the first mode to the second mode; and
execute the second mode; and
where the switch is not actuated:
stop executing the second mode.

3. The medical manipulator system according to claim 2, wherein the switch is provided at a distal-end of the operating section.

4. The medical manipulator system according to claim 1, wherein the controller is further configured to inform an operator when the calculated deviation exceeds the threshold value.

5. The medical manipulator system according to claim 1, wherein the treatment part is a forceps, the indication indicates whether or not the forceps is gripping living tissue.

6. The medical manipulator system according to claim 1, wherein the treatment part is a suction device, the indication indicates whether or not the suction device is suctioning living tissue.

7. The medical manipulator system according to claim 1, wherein the treatment part is a device capable of supplying energy to living tissue, the indication indicates whether or not the device is supplying energy to the living tissue.

8. A controller for a medical manipulator system, the controller comprising:
one or more processors configured to:
receive a request;
calculate a deviation between positions and/or orientations of a medical manipulator and positions and/or orientations of an operation device; and
receive an indication as to whether or not the medical manipulator is working on living tissue;
where the calculated deviation exceeds a threshold value and the indication indicates that the medical manipulator is not working on living tissue, the controller is further configured to:
generate a signal for minimizing the deviation; and
send the signal to the medical manipulator and/or the operation device;
wherein:
when the indication indicates that the treatment part is working on living tissue, the one or more processors are configured to set the threshold value to a first value; and
when the indication indicates that the treatment part is not working on living tissue, the one or more processors are configured to set the threshold value to a second value, the second value being larger than the first value;
wherein where the calculated deviation exceeds the threshold value the one or more processors are configured to:
generate the signal for minimizing the deviation;
send the signal to the medical manipulator and/or the operation device.

9. The controller according to claim 8, wherein the one or more processors are further configured to inform an operator when the deviation exceeds the threshold value.

10. A non-transient computer readable storage device containing instructions for controlling a medical manipulator system to perform a method, the method comprising:
receiving a request;
calculating a deviation between positions and/or orientations of a medical manipulator and positions and/or orientations of an operation device; and
receiving an indication as to whether or not the medical manipulator is working on living tissue;
wherein where the calculated deviation exceeds a threshold value and the indication indicates that the medical manipulator is not working on living tissue, the method further comprises:
generating a signal for minimizing the deviation; and
sending the signal to the medical manipulator and/or the operation device;
when the indication indicates that the treatment part is working on living tissue, setting the threshold value to a first threshold value;
when the indication indicates that the treatment part is not working on living tissue, setting the threshold value to a second threshold value, the second threshold value being larger than the first threshold value; and
where the deviation is determined to exceed the second threshold value:
generating the signal for minimizing the deviation;
sending the signal to the medical manipulator and/or the operation device.

11. The non-transient computer readable storage device according to claim 10, wherein the method further comprises informing an operator that the deviation exceeds the threshold value.

* * * * *